United States Patent [19]

Alfs et al.

[11] Patent Number: 4,461,916
[45] Date of Patent: Jul. 24, 1984

[54] PROCESS FOR THE PRODUCTION OF P-TERT-OCTYL PHENOL BY CATALYTIC ALKYLATION OF PHENOL

[75] Inventors: Helmut Alfs; Werner Boexkes; Erwin Vangermain, all of Marl, Fed. Rep. of Germany

[73] Assignee: Chemische Werke Huels A.G., Marl, Fed. Rep. of Germany

[21] Appl. No.: 454,217

[22] Filed: Dec. 29, 1982

[30] Foreign Application Priority Data

Dec. 29, 1981 [DE] Fed. Rep. of Germany ....... 3151693

[51] Int. Cl.³ .............................................. C07C 37/14
[52] U.S. Cl. .................................... 568/788; 568/785; 568/793
[58] Field of Search ........................ 568/793, 788, 785

[56] References Cited

U.S. PATENT DOCUMENTS

| | | | |
|---|---|---|---|
| 1,987,228 | 1/1935 | Brunson | 568/793 |
| 3,422,157 | 1/1969 | Kaufman et al. | 568/793 |
| 4,152,531 | 5/1979 | Hollingshead | 568/793 |
| 4,168,390 | 9/1979 | Alfs et al. | 568/793 |
| 4,198,531 | 4/1980 | Merger et al. | 568/793 |
| 4,236,033 | 11/1980 | Alfs et al. | 568/788 |

FOREIGN PATENT DOCUMENTS

| | | | |
|---|---|---|---|
| 692767 | 8/1964 | Canada | 568/793 |
| 2228749 | 12/1974 | France | 568/793 |
| 18182 | 11/1962 | Japan | 568/793 |
| 173243 | 7/1965 | U.S.S.R. | 568/793 |

OTHER PUBLICATIONS

Widdecke: Ion Exchanges as Polymeric Catalysts for the Alkylation of Aromatics, Dissertation 1978, Technical College, Braunschweig, p. 131.

Primary Examiner—Werren B. Lone
Attorney, Agent, or Firm—Millen & White

[57] ABSTRACT p-tert-octyl phenol is produced by reaction of phenol with diisobutene in the presence of an acidic ion exchanger and water, in a first stage, in a solid-bed reactor at temperatures of 110°–140° C. and under an excess pressure of up to 5 bar. The resultant dioctyl phenol formed as a by-product is alkylated in a second stage in a further solid-bed reactor with phenol in the presence of an acidic ion exchanger, and water at temperatures of 110°–140° C. and under an excess pressure of up to 5 bar to obtain additional p-tert-octyl phenol.

10 Claims, 1 Drawing Figure

PROCESS FOR THE PRODUCTION OF P-TERT-OCTYL PHENOL BY CATALYTIC ALKYLATION OF PHENOL

BACKGROUND OF THE INVENTION

This invention relates to a process for preparing p-t-octyl phenol from phenol and diisobutene by catalytic alkylation.

Alkyl phenols are manufactured industrially, primarily by catalytic alkylation of phenol with olefins. Catalysis in these Friedel-Crafts reactions takes place either homogeneously (sulfuric acid, phosphoric acid, boron trifluoride, aluminum chloride, etc.) or heterogeneously (strongly acidic cation exchangers, activated aluminas, etc.). Since homogeneous catalysis causes problems regarding environmental protection and corrosion, heterogeneous catalysis with acidic ion exchangers, especially with resins of the sulfonated, divinylbenzene-crosslinked polystryene type, is preferred. In this method, resins are employed, wherein the particle size distribution maximum is 0.3-1.3 mm. They are arranged in solid-bed reactors subjected to a flowthrough, depending on the flow velocity of the reaction mixture, from the bottom toward the top or from the top toward the bottom. The reactivity or reaction rate depends, in this connection, inter alia, on the reactants utilized, but is also dependent on the properties of the ion exchangers (degree of crosslinking, degree of sulfonation, exchange capacity, etc.). However, on the whole, despite the use of ion exchangers for catalysis on a large industrial scale, the mechanism of the reaction in dependence on the starting materials remains largely unexplored, especially in alkylations.

A step in the industrial performance of this reaction which is critical to the process is the removal of the heat of reaction. According to U.S. Pat. No. 3,422,157, this problem is solved by recycling large amounts of the reaction mixture from a first reactor back into the former via a heat exchanger, and by conducting comparatively small amounts into a second reactor. However, it is also possible, as described in French Pat. No. 2,228,749, to control the temperature by cooling coils disposed in the reactor. According to German Pat. No. 2,346,273 =U.S. Pat. No. 4,168,390=British Pat. 1,481,568), it is possible to prevent heat accumulation by affecting the activity level by the use of two series-connected reactors having different catalyst activities. This is achieved, for example, by partially replacing the hydrogen ions of the sulfo group by aluminum ions. Additionally, however, the selectivity behavior of these catalysts can be modified by exchanging H-ions with metal ions. This is frequently accompanied by a simultaneous reduction in the reaction velocity (H. Widdecke: "Ionenaustauscher als polymere Katalysatoren zur Alkylierung von Aromaten" [Ion Exchangers as Polymeric Catalysts for the Alkylation of Aromatics], Dissertation 1978, TU [Technical College] Braunschweig, page 131).

Especially remarkable is the known dependency of the heterogeneously catalyzed alkylation process on water, which latter influences the reaction velocity as well as selectivity. Thus, it has been found that when reacting phenol with propene at a reaction temperature of 75° C. and with an addition of 10% by weight of water, the phenol ether content rises by a factor of 6.3 and the conversion, within the same reaction period, drops by a factor of 3.3. The ratio of mono- to dialkyl phenol, though, which is important for economic considerations, is not altered thereby (H. Widdecke, page 125). By raising the temperature to 125° C. with the other conditions remaining the same, ether formation is greatly suppressed and the conversion rate is increased by a factor of 4.4.

The alkylation reactions with isobutene and its oligomers are likewise obscure. Thus, for example, surprisingly, no ogligomerization is observed in the alkylation of phenol as contrasted to alkylation of benzene with isobutene (H. Widdecke, page 118). In the first-mentioned reaction, phenol alkylation takes place exclusively. However, the reaction also differs from other alkylation reactions by the fact that transalkylation from o-tert-butyl phenol to the p-isomer is possible. In this connection, it is assumed that isomerization as well as transalkylation mechanisms are involved.

However, knowledge of these reaction mechanisms cannot even remotely explain the experimental results obtained in the alkylation of phenol with diisobutene. It has been found in this reaction that p-tert-butyl phenol is formed almost quantitatively rather than, as actually expected, primarily p-tert-octyl phenol. Again, only suppositions can be made regarding the course of this reaction. These make it appear possible that the first step is cleavage of the diisobutene molecule, or a disproportionation of the initially formed octyl phenol. The formation of butyl phenol can be suppressed by the addition of 1-2% of water, based on the amount of phenol utilized, at reaction temperatures of 85°-110° C., especially 100°-105° C. (French Pat. No. 2,228,749), the catalyst having previously been impregnated additionally with 10-15% of its weight of water. Under these reaction conditions, however, the reaction velocity, as is expected, is very low due to the inhibitory effect of the water; in addition, the proportion of undesired dialkyl phenols is relatively high. At temperatures of between 120° and 130° C. and without addition of water, only very small amounts of octyl phenol are obtained in the process of French Pat. No. 2,228,749, but p-tert-butyl phenol is formed in a high yield (94-96%).

SUMMARY OF THE INVENTION

Accordingly, it is an object of this invention to provide a process which shortens the uneconomically long residence times of the prior art and avoids the formation of undesired by-products, such as p-tert-butyl phenol and dialkyl phenols.

Upon further study of the specification and appended claims, further objects and advantages of this invention will become apparent to those skilled in the art.

These objects have been attained by this invention by providing a process for the production of p-tert-octyl phenol by reacting phenol with diisobutene in the presence of an acidic ion exchanger with the addition of water, comprising conducting the reaction, in a first stage, with the addition of water in a solid-bed reactor at temperatures of 110°-140° C. under an excess pressure of up to 5 bar, and in a second stage, reacting the dioctyl phenol obtained as a by-product in another solid-bed reactor with phenol in the presence of an acidic ion exchanger with the addition of water at temperatures of 110°-140° C. and under an excess pressure of up to 5 bar to obtain p-tert-octyl phenol.

BRIEF DESCRIPTION OF THE DRAWING

Various other objects, features and attendant advantages of the present invention will be more fully appreciated as the same becomes better understood when considered in conjunction with the accompanying drawings and wherein.

DETAILED DISCUSSION

Figure 1:
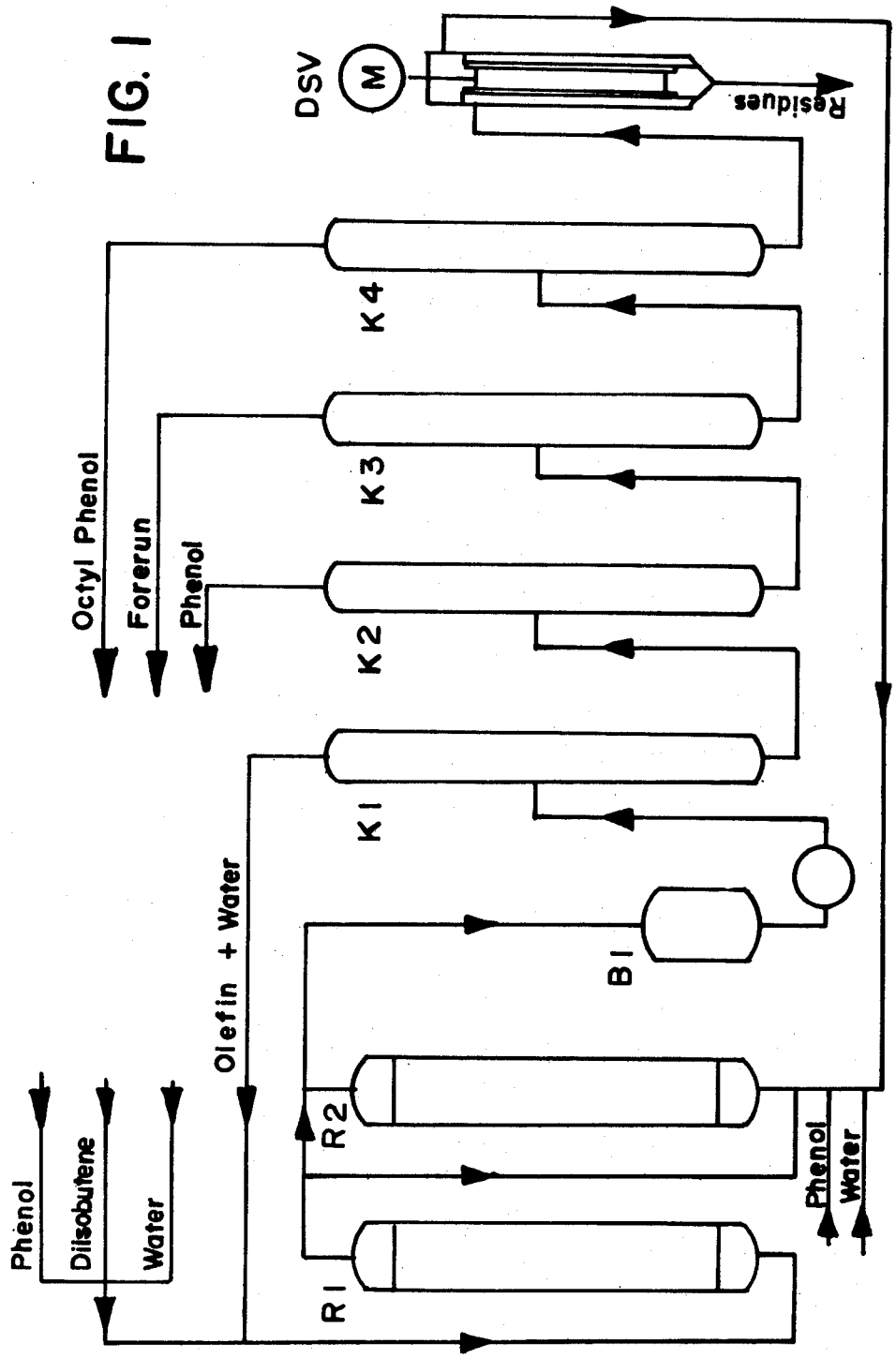
FIG. 1 depicts one configuration for continuously performing the process of this invention.

The diisobutene used in the reaction of this invention is the conventional industrially available product which is usually a mixture of isomers, e.g. 70–75 wt. % of $C(CH_3)_3$—$CH_2$—$C(CH_3)$=$CH_2$, 20–25 wt. % of $C(CH_3)_3$—$CH$=$C(CH_3)_2$; and other to a lesser degree, e.g. $CH(CH_3)_2$—$C(CH_3)$=$C(CH_3)_2$, up to 3 wt. % See, e.g., (safety date, EC, Erdölchemie GmbH) whose disclosures are incorporated by reference herein. Correspondingly, the p-tert-octyl phenol product is usually

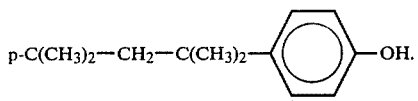

The dioctyl phenol product has two such groups in two positions of the ring, usually in the 2,4-positions.

Surprisingly, the process of this invention produces p-tert-octyl phenol of high purity with short residence times and with high space-time yields.

It is known that a temperature rise, though normally leading to an increase in the reaction velocity, also accelerates the concomitant formation of by-products, such as, for example, in the alkylation of phenol with diisobutene, the undesired formation of p-tert-butyl phenol. An increase in pressure raises the solubility of the volatile components, such as isobutene, in the liquid phase. Therefore, it had to be assumed that a rise in pressure would likewise promote the formation of p-tert-butyl phenol. It was thus especially surprising that with a simultaneous increase in temperature and pressure, in the presence of water, p-tert-octyl phenol is obtained in a high yield with an only minor quantity of p-tert-butyl phnenol product. Without adding water, higher proportions of butyl phenol are obtained (see Comparative Examples A through D).

As compared with the method in French Pat. No. 2,228,749, a substantially higher space-time yield of p-octyl phenol is achieved with the process of this invention. While Example 1 of French Pat. No. 2,228,749 yields, by calculation, only a space-time yield of 0.65 kg of p-octyl phenol/(1 of catalyst·h), the process of this invention attains space-time yields of, e.g., 8.62 kg/(1 of catalyst·h); see, e.g., Example 4. Generally, space-time yields are 4–10 kg/(1 of catalyst·h).

The dioctyl phenol formed as an undesired by-product is further reacted to form p-tert-octyl phenol in a second stage in an additional reactor containing phenol in the presence of an acidic ion exchanger with the addition of water at temperatures of 110°–140° C. and under an excess [gauge] pressure of up to 5 bar. Surprisingly, this reaction in the presence of water produces essentially only p-tert-octyl phenol (see Examples 1–4), whereas, without water, p-tert-butyl phenol is obtained as the primary product (see Comparative Examples A through D).

The process of this invention can be conducted continuously or discontinuously. Suitable catalysts include acidic ion exchangers, especially resins of the sulfonated, divinylbenzene-crosslinked polystyrene type, and equivalents as disclosed in the prior art, e.g., the references discussed above. These catalysts are utilized in both stages generally in amounts of 5–8% by weight, based on the amount of phenol utilized and/or on the hourly throughput of phenol. They are used in the dry state, as distinguished from the process in French Pat. No. 2,228,749.

In the first stage, the molar ratio of phenol to diisobutene is generally 1:1 to 8:1, preferably up to 2:1; in the second stage, the molar ratio of phenol to dioctyl phenol is generally 1:1 to 8:1, preferably 2:1 to 3:1. An addition of 1–5% of water, based on the total weight of the starting mixture, is employed in both reaction stages. Preferably, 2–3% of water is added.

The reaction takes place at temperatures of 110°–140° C., preferably 115°–130° C. under an excess (i.e., super-atmospheric) pressure of up to 5 bar, preferably 1.5–2.5 bar. The reaction period or residence time is generally 3–60 minutes, preferably 8–12 minutes.

The simplified flow chart of FIG. 1 shows a continuous performance of the process.

The two reactors R1 and R2 are fully conventional solid-bed reactors and are filled with an acidic ion exchanger. Phenol, diisobutene, and water are introduced from storage tanks into reactor R1. The exiting reaction mixture is transferred via a crude product discharge tank B1 into the distillation section where, in the first column K1, olefin and water are first of all separated and recycled to a point upstream of the first reactor. In the second column K2, phenol with the thus-formed butyl phenols is withdrawn overhead and subjected to processing. The sump product is separated in a further column K3 into a so-called forerun, primarily containing low-boiling octyl phenol isomers, and into p-tert-octyl phenol with the produced polyalkyl phenols. Another column K4 yields the pure product at its head; the fraction withdrawn from the column sump is processed in a conventional thin-film evaporator (DSV, M is the motor). The dioctyl phenol obtained as a distillate is recycled to a point upstream of the second reactor R2 for transalkylation. Into this transalkylation reactor, phenol and water are additionally introduced. The reaction mixture from R2 is introduced into the crude product discharge tank B1 and then worked up as described in the distillation plant. All of the conditions in this process are selected using fully conventional considerations.

Another advantage of the process is that a very pure p-tert-octyl phenol is obtained having a setting or solidification point of about 80° C. This pure p-tert-octyl phenol, obtained in a high yield, can be utilized for its conventional purposes, e.g., for the production of emulsifiers, detergent raw materials, and phenolic resins. See, e.g. Stache "Tensid-Taschenbuch", (1979), Hansa-Verlag, page A 36.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the following examples, all temperatures are set forth uncorrected in degrees Celsius; unless otherwise indicated, all parts and percentages are by weight.

EXAMPLES 1-3

(a) First Stage

The reaction is performed discontinuously in a stirred flask equipped with contact thermometer and reflux condenser, under the conditions indicated in Table 1. The flask is charged with 90 g of a sulfonated polystyrene ion exchange resin in the H-form, crosslinked with divinylbenzene to an extent of 8% by weight and having an activity of 4.6 meg/g catalyst, and 282 g of phenol and 168 g of diisobutene (molar ratio phenol:diisobutene=2:1) and 9 g of water (2% by weight, based on the mixture of phenol-diisobutene) is added thereto. After a reaction period of 15 minutes, the crude product is separated from the catalyst by filtration and worked up by distillation in a manner known per se without any pretreatment, thus obtaining a p-octyl phenol having a very high degree of purity (setting point 80.2° C.).

TABLE 1

| Example | Temp. °C. | Pressure bar | Conversion % | Composition (% by Weight, Calculated Free of Phenol) | | | |
|---|---|---|---|---|---|---|---|
| | | | | Butyl Phenol | Octyl Phenol | Dioctyl Phenol | Remainder |
| 1a | 110 | 1.5 | 79.1 | 4.1 | 85.8 | 5.3 | Inter- |
| 2a | 110 | 2.5 | 84.0 | 3.9 | 86.8 | 4.5 | mediate |
| 3a | 130 | 2.3 | 88.5 | 8.7 | 86.5 | 4.75 | Runs |

(b) Second State

The reaction in the second stage likewise takes place discontinuously in a stirred flask equipped with contact thermometer and reflux condenser, under the conditions indicated in Table 2. The flask is charged with 75 g of the strongly acidic ion exchanger utilized in the first stage, and 446 g of phenol and 377 g of the dioctyl phenol obtained in Examples 1(a) through 3(a) (molar ratio dioctyl phenol:phenol=1:4) and 16 g of water (2.0% by weight of water, based on the mixture of phenol-dioctyl phenol) is added thereto. After a reaction period of 60 minutes, the mixture is conventionally worked up without any pretreatment.

TABLE 2

| Example | Temp. °C. | Pressure bar | Conversion % | Composition (% by Weight, Calculated Free of Phenol) | | |
|---|---|---|---|---|---|---|
| | | | | Butyl Phenol | Octyl Phenol | Dioctyl Phenol |
| 1b | 110 | 1.5 | 99.2 | 0.99 | 67.6 | 30.0 |
| 2b | 110 | 2.5 | 99.4 | 2.09 | 64.1 | 32.8 |
| 3b | 130 | 2.3 | 64.0 | 3.7 | 55.8 | 34.4 |

EXAMPLE 4

Reactor R1 (see FIG. 1) is charged with 70 kg ($\triangleq$ 87 l) of the strongly acidic ion exchanger utilized in Examples 1-3, and

| | |
|---|---|
| 760 kg/h | phenol |
| 458 kg/h | diisobutene and |
| 23 kg/h | water | are added thereto. The temperature of the reaction mixture before entering the reactor is controlled so that the outlet temperature is 130° C.; the pressure is maintained at 2.3 bar. The crude alkylate is worked up conventionally in columns K1 through K4, thus obtaining 750 kg of p-octyl phenol/h. The dioctyl phenol obtained in the subsequent thin-film evaporator (DSV) is recycled to a point upstream of the second reactor R2 wherein the dioctyl phenol is transalkylated according to the disclosure of Examples 1(b) through 3(b) with phenol and water at 130° C. and under 2.3 bar. The overall space-time yield is 8.62 kg/(1 of catalyst·h).

COMPARATIVE EXAMPLES A-D (a) First Stage

According to the disclosure of Examples 1-3, the amounts of phenol and diisobutene indicated therein are reacted in the presence of the strongly acidic ion exchanger described therein and optionally in the presence of water. The working-up step is performed in correspondence with the disclosure of Examples 1-3. The results are compiled in Tables 3 and 4. At lower temperatures under atmospheric pressure, considerably lower conversion rates are obtained. Without the addition of water, the proportion of undesired butyl phenol is substantially higher.

(b) Second Stage

The reaction of dioctyl phenol with phenol likewise takes place according to the description of Examples 1-3, but without adding water.

TABLE 3

| Comparative Example | Water % by Wt. | Temp. °C. | Pressure bar | Conversion % | Composition (% by Weight Calculated Free of Phenol) | | |
|---|---|---|---|---|---|---|---|
| | | | | | Butyl Phenol | Octyl Phenol | Dioctyl Phenol |
| $A_1$ | 2 | 90 | 1 | 37.2 | 8.4 | 82.9 | 6.0 |
| $B_1$ | 0 | 90 | 1 | 34.4 | 14.1 | 81.5 | 2.2 |
| $C_1$ | 0 | 110 | 1.4 | 80.5 | 10.4 | 84.4 | 2.3 |
| $D_1$ | 0 | 130 | 2.1 | 94.1 | 28.6 | 68.8 | 2.5 |

TABLE 4

| Comparative Example | Temp. °C. | Pressure bar | Conversion % | Composition (% by Weight, Calculated Free of Phenol) | | |
|---|---|---|---|---|---|---|
| | | | | Butyl Phenol | Octyl Phenol | Dioctyl Phenol |
| $D_2$ | 130 | 2.3 | 99.7 | 74.7 | 18.9 | 0.4 |

What is claimed is:

1. A process for producing p-tert-octyl phenol comprising, in a first stage, in a solid-bed reactor, reacting phenol with diisobutene in a molar ratio of phenol to diisobutene of 1:1 to 8:1, in the presence of a catalytic amount of an acidic ion exchanger and 1-5 wt. % of water based on the total weight of the starting mixture, at a temperature of 110°-140° C. and under a superatmospheric pressure of up to 5 bar, thereby producing p-tert-octyl phenol and a dioctyl phenol by-product; and in a second stage, reacting the by-product dioctyl phenol in a solid-bed reactor with phenol in a molar ratio of phenol to dioctyl phenol of 1:1 to 8:1, in the presence of a catalytic amount of an acidic ion exchanger and 1-5 wt. % of water based on the total weight of the starting mixture, at a temperature of 110°-140° C. and under a superatomospheric pressure of up to 5 bar to obtain additional p-tert-octyl phenol.

2. A process of claim 1 wherein the amount of acidic ion exchanger in both stages is 5-8% by weight based on the amount of phenol used.

3. A process of claim 1 wherein the process is performed continuously and a different solid-like reactor is utilized ine each stage.

4. A process of claim 1 wherein the process is performed batchwise.

5. A process of claim 1 wherein the molar ratio of phenol to diisobutene in the first stage is 1:1 to 2:1 and the molar ratio of phenol to dioctylphenol in the second stage is 2:1 to 3:1.

6. A process of claim 1 wherein the amount of water added in each step is 2-3 wt. % on the same basis.

7. A process of claim 1 wherein the temperature in each stage is 115°-130° C.

8. A process of claim 1 wherein the pressure in each stage is 1.5 to 2.5 bar.

9. A process of claim 4 wherein a different solid bed reactor is used in each stage.

10. A process of claim 1 wherein prior to the second stage, the dioctylphenol by-product is removed from the first stage reaction product by distillation.

* * * * *